United States Patent
Noguchi et al.

[11] Patent Number: 5,098,191
[45] Date of Patent: Mar. 24, 1992

[54] METHOD OF INSPECTING RETICLES AND APPARATUS THEREFOR

[75] Inventors: Minori Noguchi; Hiroaki Shishido; Mitsuyoshi Koizumi; Nobuyuki Akiyama; Toshihilo Nakata, all of Yokohama, Japan

[73] Assignee: Hitachi, Ltd., Tokyo, Japan

[21] Appl. No.: 424,196

[22] Filed: Oct. 19, 1989

[30] Foreign Application Priority Data

Oct. 24, 1988 [JP] Japan .................. 63-266036

[51] Int. Cl.$^5$ .............................. G01N 21/88
[52] U.S. Cl. ................... 356/394; 356/237; 356/239
[58] Field of Search ........... 356/237, 239, 394; 250/562, 572

[56] References Cited

U.S. PATENT DOCUMENTS

| | | | |
|---|---|---|---|
| 4,209,257 | 6/1980 | Uchiyama et al. | 356/394 |
| 4,330,205 | 5/1982 | Murakami et al. | |
| 4,595,289 | 6/1986 | Feldman et al. | 356/237 |
| 4,952,058 | 8/1990 | Noguchi et al. | 356/237 |
| 5,957,367 | 9/1990 | Dulman | 356/394 X |

FOREIGN PATENT DOCUMENTS 139278 8/1983 Japan .

*Primary Examiner*—Vincent P. McGraw
*Attorney, Agent, or Firm*—Antonelli, Terry, Stout & Kraus

[57] ABSTRACT

Method of inspecting reticles and an apparatus therefor, where means for holding and transferring an inspected reticle and a standard reticle respectively, means for illuminating light with spatial coherency adjusted onto both reticles respectively, and an objective lens for collecting transmitted light or reflected light from the illuminated body produced by the illuminating, are installed on respective Fourier transformation surfaces of both reticle surfaces, and a light blocking plate for blocking light corresponding to the adjusted spatial coherency is installed, and electric signals obtained are compared thereby a defect or a foreign substance existing on the inspected reticle can be detected.

18 Claims, 9 Drawing Sheets

METHOD OF INSPECTING RETICLES AND APPARATUS THEREFOR

BACKGROUND OF THE INVENTION

The present invention relates to method of inspecting reticles and an apparatus therefor, wherein in exposure process of a reticle and a mask to be used for manufacturing an LSI or a print board, foreign substance or defect on the reticle and the mask is detected before pattern on the reticle and the mask is transferred onto a wafer.

In the exposure process used during manufacturing an LSI, a chromium pattern on a thick board called a reticle is printed and transferred to a semiconductor wafer. In this process, when foreign substance and defect exist on the reticle, since the pattern cannot be transferred to the semiconductor wafer exactly, all LSI chips become a defective unit. Consequently, inspection of foreign substance and defect before the exposure is inevitable in the control of the reticle.

In addition to this, since the LSI is highly integrated in recent years and therefore the pattern becomes fine, a smaller foreign substance becomes a problem attendant upon this. Also foreign substance of a flat thin film is caused by residue of a resist during manufacturing the reticle, unfinished etching of chromium or chromium oxide for the pattern forming, and impurity melted in the reticle washing liquid and aggregated during the washing and drying. This foreign substance of the flat thin film becomes a problem, and the number of such foreign substance is apt to increase more and more.

In the prior art, an apparatus for inspecting the foreign substance and defect is proposed, as disclosed in Japanese patent application laid-open No. 65428/1984 for example, comprising means for illuminating and scanning laser light to the substrate obliquely, a first lens installed to the upper side of the substrate so as to align the illuminated point of the laser light nearly to the focal plane for collecting the scattered light of the laser light, a light blocking plate installed to a Fourier transformation plane of the first lens for blocking regular scattered light from the substrate pattern, a slit installed to the focal point of a second lens to perform inverse Fourier transformation of the scattered light from foreign substance obtained through the light blocking plate for blocking the scattered light from position other than the illumination point of the laser light on the substrate, and a light receiving unit for receiving the scattered light coming from the foreign substance through the slit.

In this proposal, paying attention to that pattern is generally constituted in the same direction or in combination of several different directions within the visual field, diffraction light by the pattern in this direction is removed by the space filter installed to the Fourier transformation plane, thereby only the reflected light from the foreign substance is emphasized and removed.

Also in the prior art, as disclosed in Japanese patent application laid-open No. 139278/1983 for example, method for comparing data detected using an illuminating and detecting optical system similar to the exposure unit with data of a standard reticle or data in the design and for detecting the defect is proposed.

This method is in that data detected using the detecting optical system is binarized and compared with the binary data of the pattern estimated from the design data.

Further, the prior art is disclosed in U.S. Pat. No. 4,595,289 or U.S. Pat. No. 4,330,205.

Among the above-mentioned prior art, Japanese patent application laid-open No. 65428/1984 is characterized in that reflected light from a foreign substance is separated by a light blocking plate from reflected light from a pattern and only the reflected light from the foreign substance is detected by the slit, and that since the foreign substance is detected by the binarization method, the detecting mechanism is simplified. On the other hand, however, since the foreign substance is detected by illumination of laser light from oblique upper direction being different from the original exposure unit, so to speak, by indirect illumination, only the reflected light from the chromium pattern of specific angle is blocked but the foreign substance from all chromium pattern cannot be discriminated.

Also in the case of detecting by indirect means as above described, foreign substance without producing actual damage (hereinafter referred to as "false alarm") also may be detected. Particularly the pattern becomes fine and the number of foreign substances producing a problem is increased but the number of foreign substances producing no actual damage is also increased, thereby the number of false alarms is increased, and check regarding whether the detected foreign substance produces a problem or not, analysis and removing of the foreign substance and other works are increased and therefore the working efficiency is significantly deteriorated.

Among the above-mentioned prior art, Japanese patent application laid-open No. 139278/1983 is characterized in that since the optical system similar to the exposure unit is provided, constitution of the optical system is simplified in comparison to the prior art. On the other hand, however, a problem exists in that the image signal processing system for comparing data is complicated in comparison to the prior art and much time is required for the inspection.

The reference data is binary image, but since detection signal must be detected by tone image of multiple values due to limitation of the resolving power of the optical system, the detection signal is binarized and compared. During the binarization, even true pattern is binarized in the shape different from the reference pattern, which causes increase of the false alarms. In order to eliminate the false alarm, since algorithm is adopted where difference of several pixels is not made defect, a problem exists in that defect as large as several pixels may be overlooked. If the pixel size is made small in order to increase the resolving power as the measure for the overlooking, a problem exists in that much time is required for the inspection.

Method disclosed in U.S. Pat. No. 4,595,289 is according to comparison inspection using dark-field illumination, but even by this method, a problem exists in that a plurality of circuit corner portions enter one pixel of the detector, and when the scattered light signal from the circuit pattern becomes larger, it is difficult to decrease influence of the alignment error. That is, since the number of the circuit pattern corners detected by one pixel is varied due to misalignment, the signal level detected by corresponding one pixel of two detection systems comparing with each other is significantly varied.

U.S. Pat. No. 4,330,205 relates to an apparatus for detecting optical defects using laser beam, but this also does not provide a simple and effective detector by the comparison detection as in the present invention.

SUMMARY OF THE INVENTION

An object of the invention is to provide method of inspecting reticles and an apparatus therefor, wherein in order to solve respective problems in the prior art, only fine foreign substances or fine defects producing actual damage can be separated from a chromium pattern existing at arbitrary angle and detected.

In order to attain the foregoing object, in the present invention, means for holding and transferring an inspected reticle and a standard reticle respectively, means for illuminating light with adjusted spatial coherency to both reticles respectively, and an objective lens for collecting transmission light or reflected light from the illuminated substance produced by illumination from respective illuminating means, are installed to a Fourier transformation surface of the respective reticle surfaces, and light corresponding to the adjusted spatial coherency is blocked by a light blocking plate and the obtained electrical signals relating to the inspected reticle and the standard reticle are compared respectively, thereby defects or foreign substances existing on the inspected reticle can be detected.

Furthermore, the object can be attained by providing a standard reticle inspection data generating unit having equivalent constitution to the inspection apparatus of the reticle to be inspected or a standard reticle inspection data generating unit having function of converting the design data into inspection data inspected by the inspection unit of the reticle to be inspected, and a detecting means of defects or foreign substances for comparing electric signals detected from the detector of the inspected reticle of the inspection apparatus of the reticle to be inspected with electric signals outputted from the standard reticle inspection data generating unit and eliminating signals obtained from pattern on the reticle and actualizing and detecting the defects or the foreign substances existing on the reticle to be inspected.

BRIEF DESCRIPTION OF THE DRAWINGS

FIGS. 8a and 8b through 12 are diagrams illustrating waveform of output signal of the detector 51 at inspected reticle side and standard reticle side shown in FIG. 1;

DESCRIPTION OF THE PREFERRED EMBODIMENTS

Figure 1:
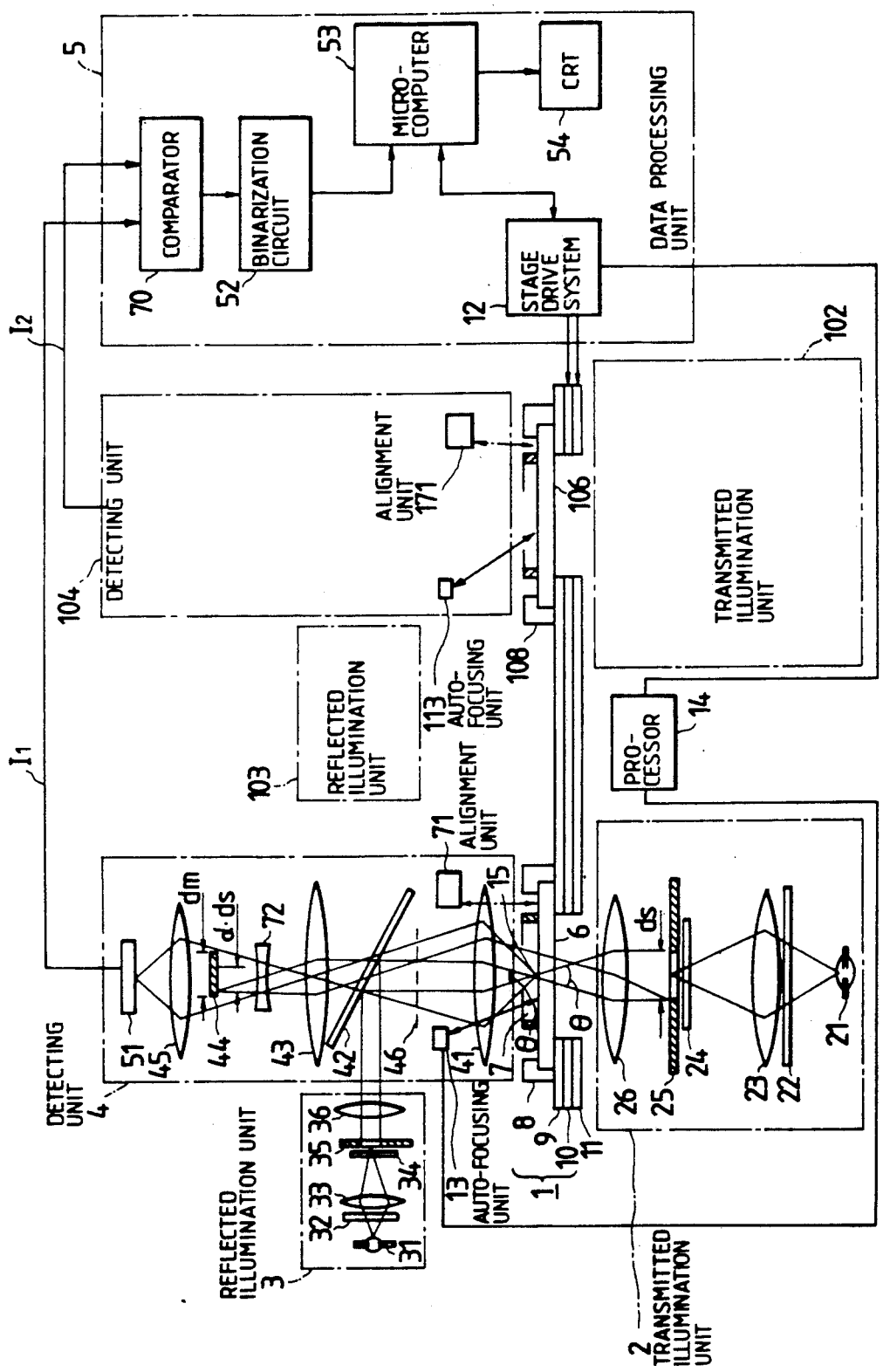
FIG. 1 is a schematic constitution diagram illustrating an embodiment of the invention.

The present invention pays attention to that luminous flux contributing to imaging is diffracted and scattered by a foreign substance and defect thereby the transfer failure due to the foreign substance and the defect is generated.

In general, numerical aperture (hereinafter referred to as "N.A.") at entrance side (body side) of a reduction projection lens is designed to value obtaining resolution being necessary and sufficient for imaging a pattern on a reticle. Consequently, luminous flux contributing to the imaging of the pattern passes through an aperture at entrance side of the reduction projection lens, but luminous flux passing through the outside of the aperture does not contribute to the imaging of the pattern. If a fine foreign substance exists, the luminous flux scattered and diffracted by the foreign substance passes through the outside from the entrance N.A. of the reduction projection lens and therefore obstructs the imaging of the pattern.

This point can be further understood, for example, from description of "Response Function of Optical System having Space Filter" in "Wave Optics" by Kubota, pp. *387-389*. That is, the reference describes that a disk-shaped space filter is held on a Fourier transformation surface of the imaging optical system, thereby a pattern having the space frequency determined by the diameter of the disk-shaped space filter, for example, the specific frequency determined by amount of radius d' when the inside of the lens is covered by circle of the radius d', cannot be resolved. Consequently, the description can be applied to the present object where difference of the space frequency between the pattern and the foreign substance, in other words, difference of size between the pattern and the foreign substance is utilized and only the foreign substance is detected.

The present invention uses an illumination system equivalent to illumination system utilizing the above-mentioned principle and used in an exposure unit and an objective lens having larger N.A. than that of the reduction projection lens, and among luminous flux incident to the objective lens, the same area as the entrance N.A. of the reduction projection lens, i.e., the diffraction light is blocked by the blocking plate, thereby only the scattered light from the foreign substance can be taken.

Consequently, in the invention, luminous flux scattered and diffracted by a foreign substance and a defect and passing through the inside of the aperture on the outside of the aperture at entrance side of the reduction projection lens of the exposure unit can be only selected and detected, thereby only the foreign substance producing actual damage can be discriminated from the pattern and detected.

When the resolution of the foreign substance is reduced, information of the scattered light from the pattern corner spreads in the whole one pixel of the detector, thereby influence of the misalignment becomes small and the foreign substance can be detected stably.

In the standard reticle detection data generating unit, using software or an electric circuit to the binary pattern image generated from the design data, space filter processing or convolution integral having the transfer function equivalent to the inspected reticle inspecting unit is applied ("Introduction to Computer Image Processing" by H. Tamura, pp. 47-49) thereby the standard reticle inspection data of multiple values is generated. The standard reticle inspection data and the inspection data of the inspected reticle inspecting unit are compared in the data of multiple values, thereby error produced during the binarization of the inspection data of the inspected reticle inspecting unit (quantization error in the plane direction) can be eliminated and the plane alarm is eliminated and the fine defect of several pixels can be detected.

In this case, even if the circular space filter within the inspected reticle inspecting unit is not used, the above-mentioned problem can be solved if the processing in the standard reticle inspection data generating unit is matched with the transfer function in the case of no space filter simultaneously.

An embodiment of the present invention will now be described referring to FIGS. 1 through 4.

As shown in FIG. 1, an apparatus for inspecting a defect or a foreign substance according to the invention comprises a sample holder unit 1, transmitted illumination units 2 and 102, reflected illumination units 3 and 103, detecting units 4 and 104, and a data processing unit 5.

The sample holder unit 1 comprises Z stage 9 for fixing a reticle 6 having a pelicle 7 by a fixing means 8 and scanning it in Z direction, X stage 10 for scanning the reticle 6 through the Z stage 9 in X direction, Y stage 11 for scanning the reticle 6 through the X stage 10 and the Z stage 9 in Y direction, a stage drive system 12 for driving each of the stages 9, 10, 11, an auto-focusing unit 13 for detecting the position in Z direction of the reticle 6, and a processor 14 for driving the stage drive system 12 by command from the auto-focusing unit 13, wherein the reticle 6 during the inspection can be focused always with accuracy at necessary minimum.

The stage 10 is constituted to perform periodic motion of maximum speed of about 1 mm/s and amplitude 200 mm in ½ period of uniform acceleration time of about 0.1 second, uniform motion of 0.1 second and uniform deceleration time of 0.1 second.

The Y stage 11 is constituted to transfer the reticle 6 in Y direction in synchronization with the uniform acceleration time and the uniform deceleration time of the X stage 10 at step of every 0.15 mm. If the reticle 6 is transferred 670 times during one inspection time, it can be transferred 100 mm in about 130 seconds thereby the area of 100 mm square can be scanned in about 130 seconds.

Although the X and Y stages 10, 11 are carried out in the embodiment, the invention is not limited to this. For example, X$\theta$ stage scanning the rotational direction and the X direction may be used. Also regarding the scanning speed, an example is shown in the above description and it may, of course, be arbitrarily set if necessary.

The auto-focusing unit 13 may be that using an air micrometer or that detecting the position by laser interference method or that projecting the stripe pattern and detecting its contrast.

Since the transmitted illumination units 2 and 102 are constituted by the same components, the transmitted illumination unit 2 will be described here.

The transmitted illumination unit 2 is constituted so that g-ray (wavelength 436 mm) or i-ray (wavelength 365 mm) used in an exposure unit (not shown) is selected among luminous flux emitted from a mercury arc lamp 21 by a dichroic mirror 22, and when the light is concentrated by a condenser lens 23 onto a diffusing plate 24, the light diffused by the diffusing plate 24 is emitted from a portion limited by a circular diaphragm 25 and enters the reticle 6 and illuminates the reticle 6.

The diaphragm 25 is installed nearly at the focal position of the collimator lens 26, and image of the diaphragm 25 is focused by the collimator lens 26 and an objective lens 41 of the detecting unit 4 to position 46 shown in dash-and-dot line.

In order to attain the foregoing object of the invention, not only wavelength of the illumination light must be made the same as that of the illumination light used in the exposure unit, but also angle $\theta$ of luminous flux incident to one point 15 on the reticle 6 must be made the same. Where sin $\theta$ is defined as "spatial coherency".

In the illumination of the exposure unit, since all area on the reticle 1 must be illuminated uniformly, an optical element called an integrator assembling rod-shaped lenses is used in place of the diffusion plate 24. Since function of the integrator is basically the same as that of the diffusing plate 24 and the inspection range applied by the invention is from several hundred microns to 1.2 mm of the reticle 6, the diffusing plate 24 is sufficient.

Since the incident angle $\theta$ of luminous flux being incident onto the reticle 6 is determined by size of the integrator, i.e., diameter of the diaphragm 25 installed at the rear side of the diffusing plate 24, aperture of the diaphragm 25 is set to have the same spatial coherency as that of the illumination used in the exposure unit using the reticle 1.

Further in the exposure unit, since position of the integrator is not always set to the focal position of the collimator lens 26, the position of the diaphragm 25 need not be set always to the focal position of the collimator lens 26.

However, if it is desired that the incident angle $\theta$ of luminous flux is made constant at arbitrary position within the light illumination area on the reticle 6, and the illumination condition of the luminous flux within the measuring area is made the same and the detecting condition of the foreign substance is made the same, the diaphragm 25 is preferably set to the focal position of the collimator lens 26.

Since the reflected illumination units 3 and 103 are constituted by the same components, the reflected illumination unit 3 will be described.

The reflected illumination unit 3 is constituted so that light emitted from a mercury arc lamp 31 and passing through a dichroic mirror 32, a condenser lens 33, a diffusing plate 34 and a diaphragm 35 passes through a relay lens 36 and illuminates the reticle 6 through a half mirror 42 and an objective lens 41 of the detecting unit 4.

The objective lens 41 has the same function as that of the collimator lens 26 of the transmitted illumination unit 2.

The relay lens 36 is installed to generate an apparent diaphragm to a focal position 46 on upper side of the objective lens 41. More specifically, the real image of the diaphragm 35 is imaged to the focal position 46.

Also in the reflected illumination unit 3, similar to the transmitted illumination unit 2, aperture angle of the diaphragm 35 is determined so that wavelength of the illumination light and angle θ of luminous flux incident to any one point 15 on the reticle 6 are made the same as that of the illumination light used in the exposure unit.

Since the reflected illumination unit 3 is installed to detect a foreign substance on the chromium pattern of the reticle 6, it is unnecessary if the foreign substance on the chromium pattern need not be detected.

When the reflected illumination unit 3 and the transmitted illumination unit 2 are used simultaneously, signal from the edge of the pattern becomes large. If this becomes a problem, both units must be used separately.

Wavelength of the illumination light need not be necessarily made g-ray and i-ray, but may be other light of wide band including g-ray and i-ray. Because the foreign substance and the pattern are different in the diffraction state regarding lights of all wavelength ranges thereby the foreign substance can be discriminated from the pattern and detected even at the light of wide band.

Since the detecting units 4 and 104 are constituted by the same components, the detecting unit 4 will be described.

The detecting unit 4 comprises an objective lens 41, a half mirror 42, a field lens 43, a light blocking plate 44 and an imaging lens 45, and is constituted so that an inspection point 15 on the reticle 6 is imaged by the objective lens 41 and the imaging lens 45 to a detector 51. Also the detecting unit 4 has the field lens 43 in the vicinity of the imaging position of the objective lens 41. The field lens 43 has function that the focal position on upper side of the objective lens 41 is imaged on the circular light blocking plate 44. That is, light from the diaphragm 25 of the transmitted illumination unit 2 passes through the collimator lens 26 and the objective lens 41 and is reflected on the reticle 6, and passes again through the objective lens 41 and the field lens 46 and is imaged on the light blocking plate 44. Then the position of the light blocking plate 44 is made position of Fourier transformation of the position of the reticle 6 with respect to the position of the light source, i.e., the position of the diaphragm 25.

In this case, N.A. at side of the reticle 6 of the reduction projection lens of the exposure unit is generally set larger than the spatial coherency of the illumination system of the exposure unit (equivalent to the spatial coherency of the transmitted illumination unit 2) by about 10% through 40%, and by about 10% in most cases.

Since luminous flux passing through the outside of the aperture at entrance side of the reduction projection lens must pass through the inside of the aperture, N.A. of the objective lens 41 is made larger than N.A. of the reduction projection lens, and the light blocking plate 44 is installed so as to block luminous flux being incident within N.A. of the reduction projection lens.

Consequently, in order to attain the foregoing object of the invention, the diameter dm of the light blocking plate 44 is calculated by following expression (1).

$$dm = ds \cdot a \cdot \frac{N.A.}{\sin\theta} \cdot (1 + \delta) \qquad (1)$$

where ds is diameter of the diaphragm 25, a is magnification of the imaging system of the diaphragm 25 and the light blocking plate 44, N.A. is value at side of the reticle 6 of the reduction projection lens, and sin is spatial coherency of the exposure unit.

In this case, if $\theta = \theta s$, the detection condition of the foreign substance can be made the same. In this case, the expression (1) becomes $$dm = ds \cdot a \cdot \frac{N.A.}{\sin\theta_s} \cdot (1 + \delta) \qquad (1)'$$

It has been confirmed by the experiment that δ is clearance and may be several % (δ=0.02–0.08).

When the reticle 6 is not moved and all inspection areas on the reticle 6 are inspected simultaneously, size of the objective lens 41 is made large and the manufacturing becomes difficult in practice. In the invention, since the inspection area on the reticle 6 is limited and the reticle 6 is scanned by the sample holder unit 1 and all inspection areas can be inspected, the objective lens 41 having larger N.A. than that of the reduction projection lens in ordinary use can be used.

In order to inspect the foreign substance irrespective of whether it produces actual damage or not, size of the light blocking plate 44 need not be necessarily matched with N.A. at entrance side of the reduction projection lens used in value of the expression (1), but may be made size calculated in that $N.A./\sin\theta = 1$ is set in the expression (1) and arbitrary value δ' larger than δ by several % is used specifically. In this case, the expression (1) becomes $$dm = ds\, a\, (1 + \delta') \qquad (1)$$

Further, the spatial coherency of the illumination light need not be necessarily matched with the coherency of the exposure unit, but may be determined so that the diffraction light of 0-degree can be blocked by the light blocking plate 44. That is, size of the diaphragms 25, 35 and the light blocking plate 44 may be determined within range satisfying the expression (1).

When the reflected illumination unit 3 is not installed, even if the half mirror 42, the field lens 43 and the imaging lens 45 are omitted and the light blocking plate 44 is installed to the focal position 46 and the detector 51 is installed to the position where the field lens 43 was installed respectively, effects of the invention can be obtained. In this case, the optical system of quite simple constitution can be obtained.

The data processing unit 5 comprises a comparator 70, a binarization circuit 52, a micro computer 53 and a display means 54.

The detector 51 is formed, for example, by one-dimensional solid image pickup element of charge moving type, and the X stage 10 is scanned and signal is detected in the detector 51.

The detector 51 is not limited to one-dimensional solid image pickup element as above described, but that of two-dimensional element or single element may be used.

The comparator 70 takes signals from the detectors 51 and 151, and outputs difference of two signals.

The binarization circuit 52 previously sets the binarization threshold value, and judges whether a foreign substance exists or not.

The micro computer 53 previously sets evaluation function. That is, since whether or not a foreign substance produces actual damage being transfer failure is function of intensity of scattered light due to the foreign substance and size of the foreign substance, function of a foreign substance producing actual damage is previously evaluated, and the micro computer 53 judges whether a foreign substance producing actual damage exists or not by the evaluation function and outputs the result to the display means 54.

An apparatus for inspecting a pattern defect or a foreign substance according to the invention is constituted as above described.

Next, inspection method and its operation will be described based on FIGS. 2 through 6.

Figure 5A:
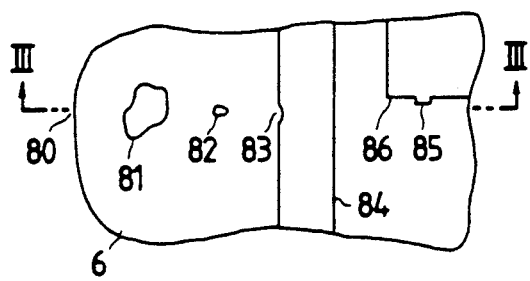
FIGS. 5a and 5b are plan views of an inspected reticle having foreign substance and defect and a standard reticle.
Figure 6A:
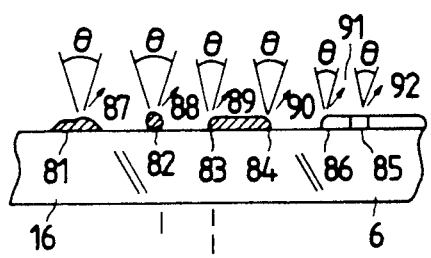
FIGS. 6a and 6b are diagrams illustrating sectional constitutions of FIGS. 5a and 5b.

A plan view of the reticle 6 as an inspection object is shown in FIG. 5a, and a sectional view in a line 80 is shown in FIG. 6a.

Figure 5B:
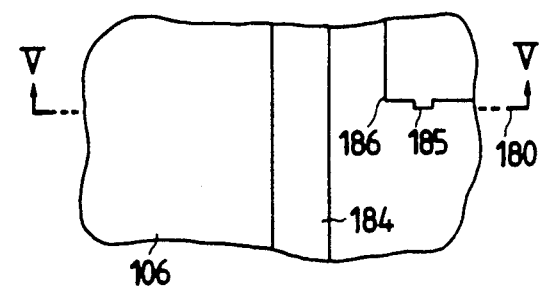
Figure 6B:
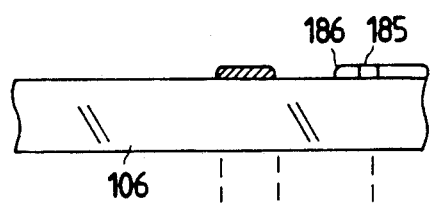

Also, a plan view of a reticle as an inspection standard is shown in FIG. 5b, and a sectional view thereof is shown in FIG. 6b.

As shown in FIG. 5a, FIG. 5b, assuming the reticles 6 and 106. in an example of the case that foreign substances 81 and 82, a pattern defect 83, edge portions 84, 184 of normal pattern, corner portions 86, 186 of normal pattern, and fine normal patterns 85, 185 existing on reticles respectively, operation of the invention will be described. The reticle 106 is a standard reticle.

Since the foreign substance 82 is fine, it scatters or diffracts the light much in comparison to the edge portion 84 of the normal pattern. That is, luminous flux 88 scattered to the outside from the range $\theta$ blocked by the light blocking plate 44 becomes more than luminous flux 90, 91 scattered to the outside from $\theta$ of the edge portion 84 and the corner portion 86. Also regarding the foreign substance 81 and the pattern defect 83, since the foreign 81 has small size, the space frequency at the periphery of the foreign substance 81 becomes high, thereby luminous flux 87 scattered to the outside from the range $\theta$ blocked by the light blocking plate 44 becomes more than luminous flux 90, 92 of the edge portion 84 and the corner portion 86.

Figure 7A:
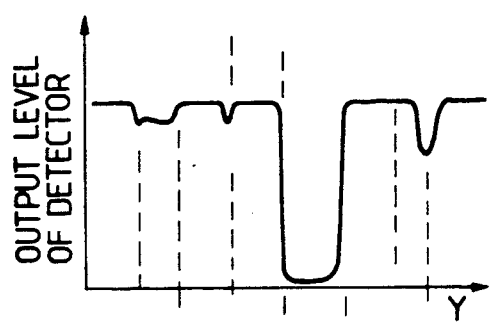
FIGS. 7a and 7b are diagrams illustrating detection signal in the prior art.
Figure 7B:
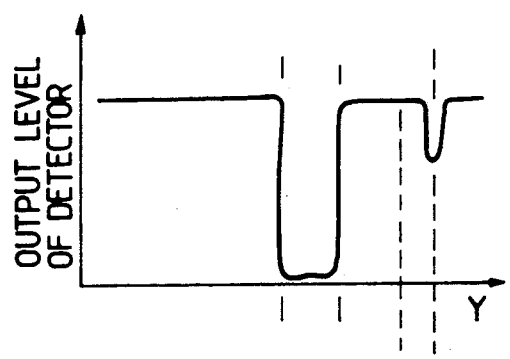
Figure 8A:
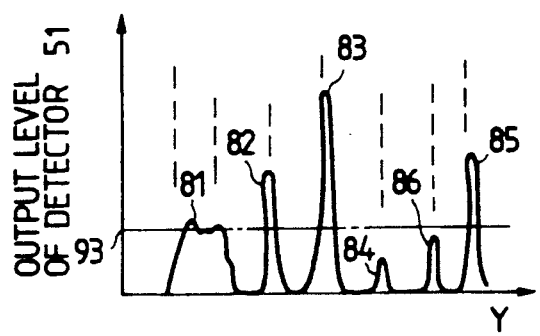
Figure 8B:
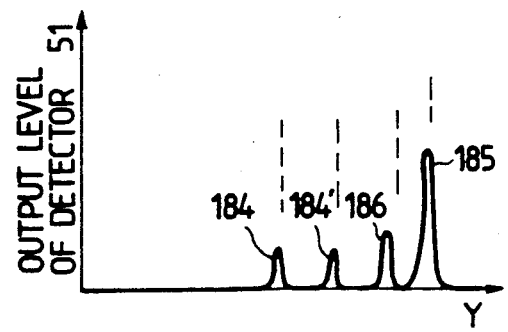

Detection signals in positions 80, 180 by the transmitted light are shown in FIG. 7a, FIG. 7b. The detection signal according to the invention has strong output at the corner portion of the foreign substance, and becomes as shown in FIG. 8a, FIG. 8b.

Consequently, in this case, if binarization is performed at threshold value 93, the foreign substances 81 and 82 can be separately detected with respect to the edge portion 84 and the corner portion 86 of the pattern.

However, an LSI becomes fine and a fine normal pattern such as a pattern 85 is used. In such pattern, since the space frequency is high, the luminous flux 92 scattered to the outside from the region $\theta$ blocked by the light blocking plate 44 becomes comparable to the foreign substances 81, 82 and the pattern defect 83 or more.

As a result, the binarization at the threshold value 93 cannot detect the pattern 92 separately from the foreign substances 81, 82 and the defect 83.

The detection signal in the detection position 180 of the inspection standard reticle in FIG. 6b is shown in FIG. 8b.

The detection signal of the inspection object reticle 6 in FIG. 8a and the detection signal of the inspection standard reticle 106 in FIG. 8b are taken, and absolute value of difference of the two signals is obtained in the comparator 70. The result is shown in FIG. 9.

Figure 9:
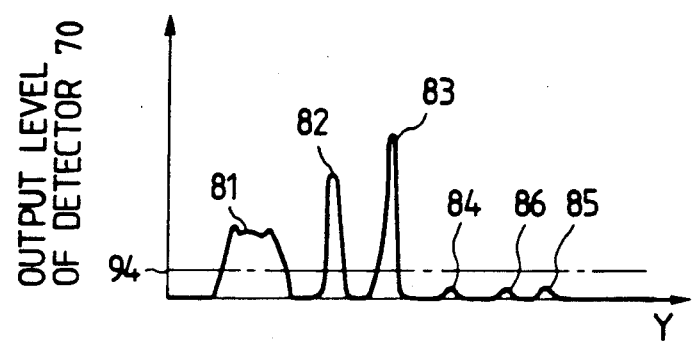

In the case of FIG. 9, if threshold value 94 is set, the foreign substances 81, 82 and the defect 83 can be discriminated from the patterns 84, 85, 86 and detected.

Figure 10:
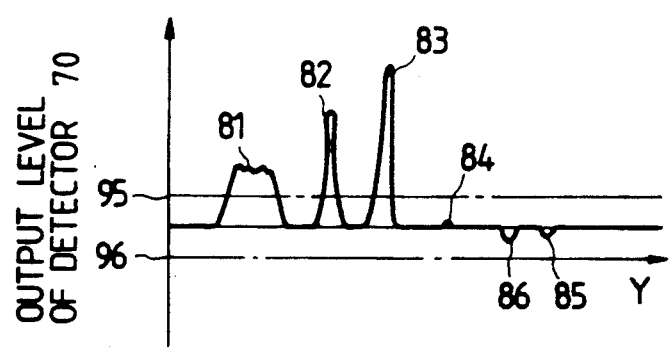

In this case, the output of the comparator 70 is outputted in absolute value of difference ($|I_1 - I_2|$) as shown in FIG. 9, but need not be necessarily limited to this. For example, it may be outputted as difference of the two circuits shown in FIG. 1 ($I_1 - I_2$). FIG. 10 shows value of the signal in FIG. 8b subtracted from the signal in FIG. 8a. When the signal in FIG. 8a is higher, the threshold value 95 detects it as a foreign substance or a defect. That is, the threshold value 95 represents that a foreign substance or a defect exists in the inspection object reticle 6 outputting the signal in FIG. 8a. On the other hand, the threshold value 96 represents that value of the signal in FIG. 8b is higher, i.e., a foreign substance or a defect exists in the standard reticle 106.

Next, operation will be described.

The inspection object reticle 6 and the standard reticle 106 drawing the same pattern are fixed respectively by fixing jigs 8 and 108 on the inspection stage 9.

The two reticles 6 and 106 detect alignment marks by alignment units 71 and 171. Based on the signals, the XY$\theta$ fine adjustment mechanisms 9, 10, 11 are moved, and perform adjustment so that the inspection object positions of the two reticles 6 and 106 are imaged on positions corresponding to the detectors 45 and 145.

Next, the X stage 10 and the Y stage 11 are scanned as above described. Then the reticles 6 and 106 are moved simultaneously. During the scanning, the focal points of the two reticles are aligned by the auto-focusing units 13 and 113 simultaneously.

Then the alignment of the two reticles is always accompanied by error $\beta$.

Figure 11:
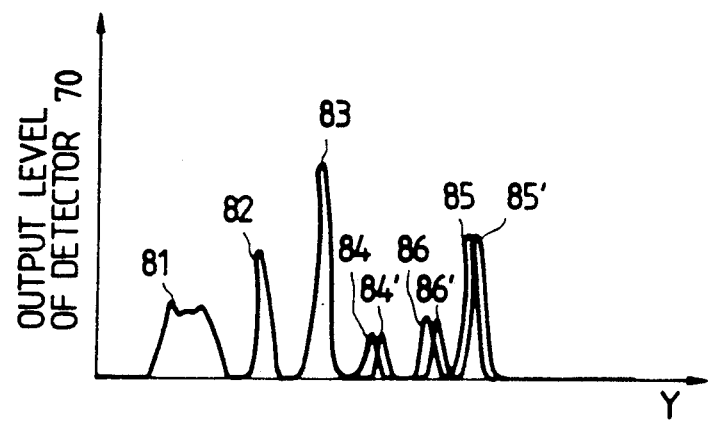
Figure 12:
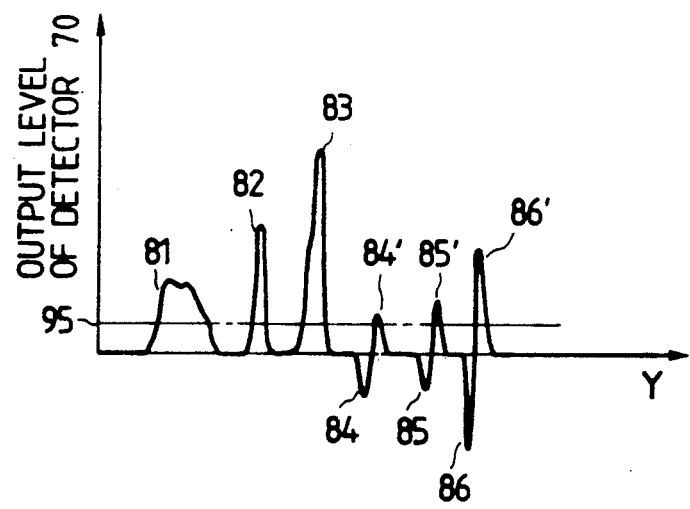

When the error $\beta$ is produced, the detection signals in FIG. 8a and FIG. 8b are overlapped as shown in FIG. 11 by the comparator 70, thereby the output of the comparator 70 becomes as shown in FIG. 12. In this case, the foreign substances 81, 82, 83 cannot be discriminated from the normal patterns 84, 85, 86 and detected by the threshold value 95.

Figure 13:
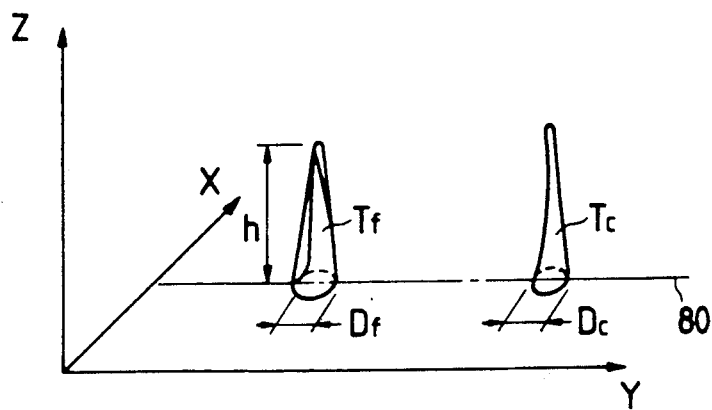
FIG. 13 is a model diagram of detecting signal detected from a pattern corner and a foreign substance according to the invention.

The allowable alignment error $\beta$ will be estimated. Image of the pattern corner portion 86 by the detection optical system becomes as shown in FIG. 13. The total output signal of the pattern corner portion 8 is made Tc, and diameter of the image of the pattern corner 86 is made Dc, and also the total output signal of the foreign substance is made T$f$, and diameter thereof is made D$f$. Detection of the pattern corner portion 86 and the foreign substance 82 by the detection pixels W$\times$W will be studied.

Variation $\Delta$Ic of the detection signal of the corner portion due to the misalignment $\delta$ becomes following expression (2). The detection waveform approximates cone of diameter Dc and height h as shown in FIG. 13, and the variation takes maximum value.

$$\Delta Ic = Tc \cdot \frac{\frac{1}{2} \cdot Dc \cdot h}{\frac{1}{3} \cdot \left(\frac{Dc}{2}\right)^2 \cdot h} = Tc \cdot \frac{6 \cdot \beta}{\pi \cdot Dc} \qquad (2)$$

($W > Df$)

Figure 14:
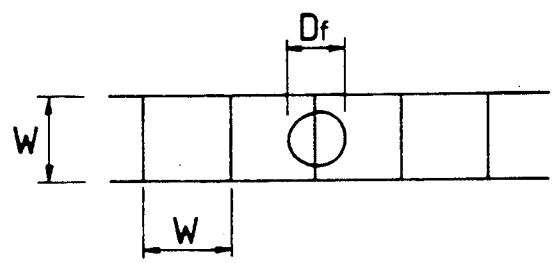
FIG. 14 is a model diagram of a foreign substance imaged on a detector.

When image of the foreign substance is imaged over adjacent detection pixels as shown in FIG. 14, the detection signal $I_f$ of the foreign substance becomes minimum as shown in following expression (3).

$$I_f = 4 \cdot T_f \quad (3)$$

From expressions (2) and (3), the alignment error $\beta$ allowable to detect the foreign substance 82 by the comparator 70 must satisfy following expression (4).

$$\Delta T_c < I_f \quad (4)$$

$$\therefore \beta < \frac{\pi}{24} \cdot \frac{T_f}{T_c} \cdot D_c \quad (4)'$$

From expression (4)', if the diameter Dc of the pattern output signal is made large, the allowable error $\beta$ can be made large. On the other hand, in order to take the whole output signal Tc of the foreign substance into one pixel of the detector efficiently, following expression (5) must be satisfied.

$$W > D_f (\simeq D_c) \quad (5)$$

Consequently, state $D_c \simeq W$ is the most efficient.

On the other hand, in order to detect the foreign substance to degree of following expression $$T_c \simeq 5 \cdot T_f \quad (6)$$

from expressions (6), (4)'

$$\beta < \frac{1}{36} \cdot D_c \quad (7)$$

In this case, in order that $\beta < 0.2$ µm, Dc becomes Dc = 7.6 µm.

That is, the resolution of the image may be reduced to 7.6 µm.

Next, how to reduce the resolution of the image will be described. The resolution of the image is set by the numerical aperture of the objective lens. Consequently, the numerical aperture may be decreased. However, if the numerical aperture is decreased, the detection signal level is also lowered. Consequently, in order to reduce the resolution without decreasing the numerical aperture, a phase filter 72 having shape as shown in FIG. 15 and FIG. 16 is installed to position of Fourier transformation of the image of FIG. 1.

Figure 15:
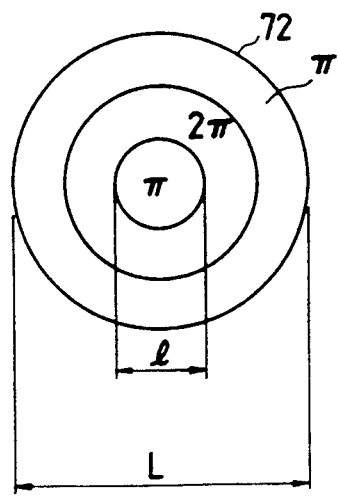
FIGS. 15 and 16 are plan views each illustrating a constitution example of a phase filter 72 shown in FIG. 1.
Figure 16:
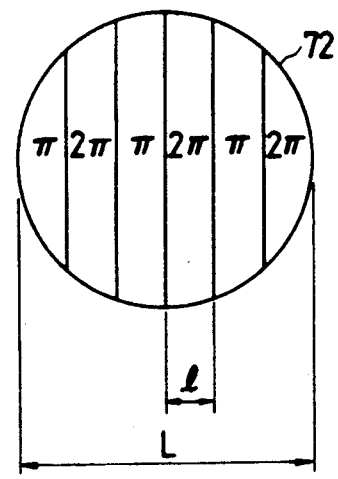

The phase filter 72 is divided in ring band-shaped parts as shown in FIG. 15, and phase of each part is varied in step of $\pi$. Also FIG. 16 shows that divided linearly. Width l of each part in this case is made about value shown in following expression, thereby the image can be widened to following $D_f$ nearly intended value.

$$D_f = 1.2 \frac{\lambda}{N.A. \frac{l}{L}} \quad (8)$$

where N. A. is numerical aperture of the objective lens, and L is size of the Fourier transformation surface.

The invention can detect a foreign substance having specific size or more by only the detecting unit 4, i.e., by only the binarization without comparing. This principle and operation will be described.

Figure 2:
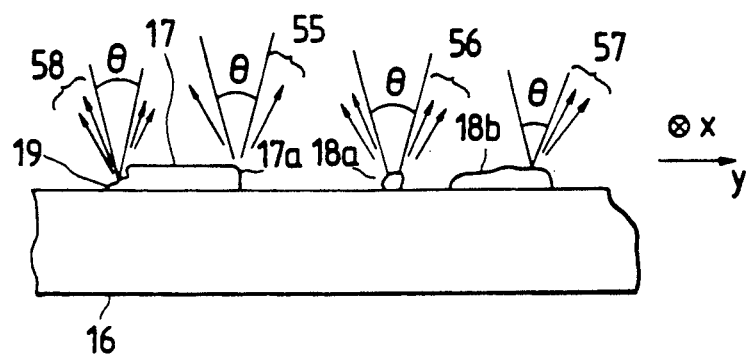
FIG. 2 is a sectional view of an inspected reticle.

As shown in FIG. 2, description will be performed regarding the case that a pattern 17, two foreign substances 18a, 18b and a defect 19 exist on a glass substrate 16. Since one small foreign substance 18a is fine, it scatters or diffracts the light much in comparison to the edge 17a of the pattern 17. That is, luminous flux 56 scattered to the outside from the range $\theta$ blocked by the light blocking plate 44 becomes more than luminous flux 55 of the edge 17a of the pattern 17.

Also regarding the defect 19 of the other large foreign substance 18b or the pattern 17, since the space frequency at the periphery is high, luminous flux 57, 58 scattered to the outside from the range $\theta$ blocked by the light blocking plate 44 becomes more than luminous flux 55 the edge 17a of the pattern 17.

Consequently, the output of the detector 51 generates output peak 59, 60, 61, 62 by each of the luminous flux 55, 56, 57, 58.

Figure 3:
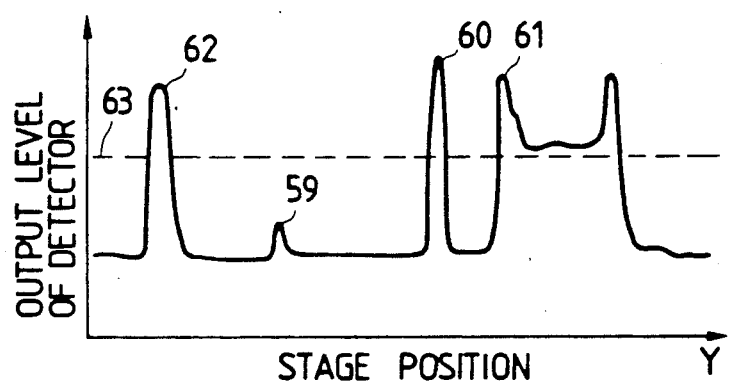
FIG. 3 is a diagram illustrating output signal of a detector 51 shown in FIG. 1.
Figure 4:
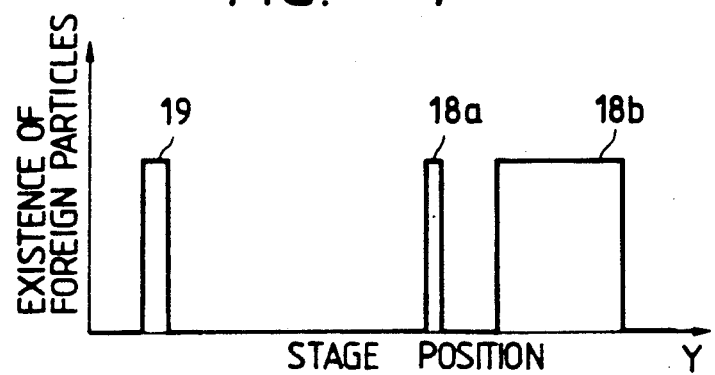
FIG. 4 is a diagram illustrating waveform of binarization signal where signal shown in FIG. 3 is binarized by a binarization circuit.

On the other hand, if threshold value 63 is set by the binarization circuit 52 as shown in FIG. 3, the output peak 60, 61, 62 in three pieces project as output being the threshold value 63 or more, thereby only the two foreign substances 18a, 18b and the defect 19 of the pattern 17 can be detected.

Coordinates of the X, Y stages 10, 11 and the level of the output peak 60, 61 are stored in the memory controlled by the micro computer 53, and the storage content is processed and outputted to the CRT 54.

Next, second and third embodiments of the invention will be described using FIGS. 17 through 18.

Figure 17:
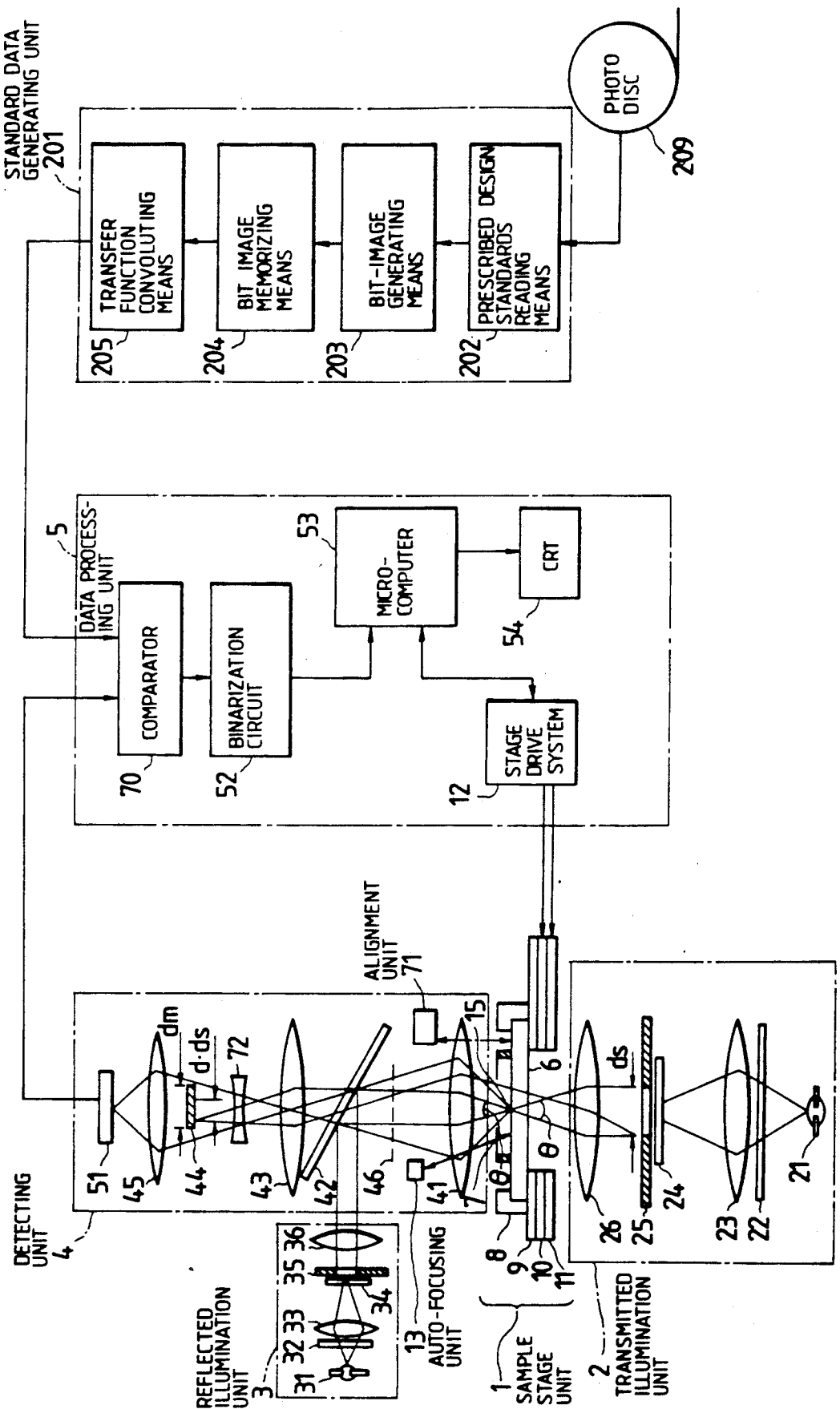
FIG. 17 is a schematic constitution diagram illustrating a second embodiment of the invention.

As shown in FIG. 17, an apparatus for inspecting a defect or a foreign substance according to the invention comprises a sample holder unit 1, a transmitted illumination unit 2, a reflected illumination unit 3, a detecting unit 4, a standard data generating unit 201 and a data processing unit 5.

Since the transmitted illumination unit 2, the reflected illumination unit 3, the detecting unit 4 and the data processing unit 5 are similar to those in constitution of the first embodiment shown in FIG. 1, the detailed description shall be omitted here. Also regarding the inspection method and its action and operation similar to that already described, the description shall be omitted here.

The second embodiment is as shown in FIG. 17, and the standard data generating unit 201 will be first described.

The standard data generating unit 201 comprises a prescribed design standards reading means 202, a bit-image generating means 203, a bit-image memorizing means 204 and a transfer function convoluting means 205.

The prescribed design data standards reading means 202 reads the design data during drawing the pattern to the reticle from an MT (magnetic tape) or a photo disk 209. The bit-image generating means 203 generates a binary pattern image from the design data, and the result is stored in the bit-image memorizing means 204. Since the bit image memorizing means 204 must read the data at high speed, a semiconductor memory such as SRAM to enable the high-speed processing is preferable therefor. In the transfer function convoluting means 205, convolution integral of the transfer function equivalent to the detecting unit 4 is performed and outputted to the data processing unit 5. In this case, for comparison with signal from the detecting unit 4 at real time, the transfer function convoluting means 205 is preferably a pipeline type as disclosed in "Automatization of Appearance Inspection" edited by the Institute of Electrical Engineers of Japan, Research Expert Committee for Automatization of Inspection, pp. 267-268, published by OHMSHA Company.

Operation action regarding the standard data generating unit 201 is as follows. In FIG. 17, the standard data generating unit 201 introduces signal equivalent to the detection signal of the standard reticle from the design data of the pattern.

The transfer function convoluting method to generate the standard reticle inspection data will be described. In "Image Optics:Corona Company" by S. Hasegawa (pp. 49, 56), regarding output image when an image passes through the optical system, gradation of image of the optical system, i.e., deterioration of the image due to the point spread function is described as follows.

When the input image to the optical system is made f (x, y), the point spread function is made h (x, y), and output is made g (x, y), $$g(x, y) = \int \int_{-\infty}^{\infty} f(x', y') h(x - x', y - y') dx' dy' \quad (9)$$

On the other hand, between spectrums $$G(u, v) = F(u, v) \cdot H(u, v) \quad (10)$$

where G (u, v), F (u, v), H (u, v) are Fourier transformation of g (x, y), f (x, y), h (x, y) respectively.

Consequently, the function h (x, y) to be convoluted by expression (9) by the input image and the output image from expression (10) in inverse Fourier transformation by following expression (11).

$$h(x, y) = \int \int_{-\infty}^{\infty} H(u, v) \cdot (2\pi j(ux + vy)) du dv \quad (11)$$

The above relation, of course, applies also when the g (x, y) is not point spread function.

Next, h (x, y) will be calculated specifically.

In the optical system, if N. A.=0.5 and use wavelength $\lambda = 0.5$ μm, convolution function becomes Fourier inverse transformation of the optical system of N. A.=0.5, i.e., a circle. This function becomes Sinc function. Thinking the case of use to component of first order, size Wc of the convolution function becomes $$Wc = 4 \times \lambda / N. A. \approx 4(\mu m) \quad (12)$$

Next, the pixel size ΔWc of the convolution filter will be thought.

ΔWc is preferably made the same as the pixel size during the pattern drawing onto the reticle.

In this case, since the binary image data generated from the design data can be subjected to covolution integral as it is, the edge portion of the pattern does not spread between the pixels of the convolution filter and the quantization error can be eliminated.

However, ΔWc is not necessarily limited to this. In order to decrease the pixel number in the whole filter area, ΔWc may be made large, and in order to raise the accuracy, ΔWc may be made small.

The pixel number $N_2$ of the convolution filter becomes $$N^2 = (W_c / \Delta W_c)^2 \quad (13)$$

Also when the circular space filter 44 as shown in FIG. 1 is used, part of the space filter is subjected to inverse Fourier transformation and the convolution function may be calculated. Size of the convolution function may be estimated according to the expression (11).

Further, although not described here, in the case of a space filter and a phase filter as disclosed in Japanese patent application No. 149516/1986, the convolution function h (X, Y) may be calculated by expression (11).

Next, the detection signal of the inspection object reticle 6 in FIG. 8a and the output signal of the standard data generating unit 201 in FIG. 8b are taken, and absolute value of difference of the two signals is obtained in the comparator 70. The result is shown in FIG. 9.

In the case of FIG. 9, if the threshold value 94 is set, the foreign substances 81, 82 and the defect 83 can be discriminated from the patterns 84, 85, 86 and detected.

In this case, the output of the comparator 70 is outputted in absolute value as shown in FIG. 9, but need not be necessarily limited to this. As shown in FIG. 10, it may be outputted as difference of two circuits. FIG. 10 shows value of the signal in FIG. 8b subtracted from the signal in FIG. 8a. When the signal in FIG. 8a is higher, the threshold value 95 detects the signal as a foreign substance or a defect. That is, the threshold value 95 represents that a foreign substance or a defect exists in the inspection object reticle 6 outputting the signal in FIG. 8a.

Next, operation will be described.

The inspection object reticle 6 is fixed by the fixing jigs 8 and 108 on the inspection stage 9. The reticle 6 detects alignment marks by the alignment mark detecting means 71 and 171. Based on the signals, the XYΘ fine adjustment mechanisms 9, 10, 11 are moved, and performs adjustment so that the inspect object position of the reticle 6 is imaged on position corresponding to the detector 45.

On the other hand, in the standard data generating unit 201, the design data of the inspected reticle 6 is set to the prescribed design standards reading means 202, and bit image is generated in the bit-image generating means 203 and stored in the bit-image memorizing means 204.

The X stage 9 and the Y stage 10 are subjected to automatic focusing and scanned as above described. At the same time, bit image of corresponding pattern is read in sequence from the bit image memorizing means 204 and processed in the transfer function convoluting means 205.

Figure 19:
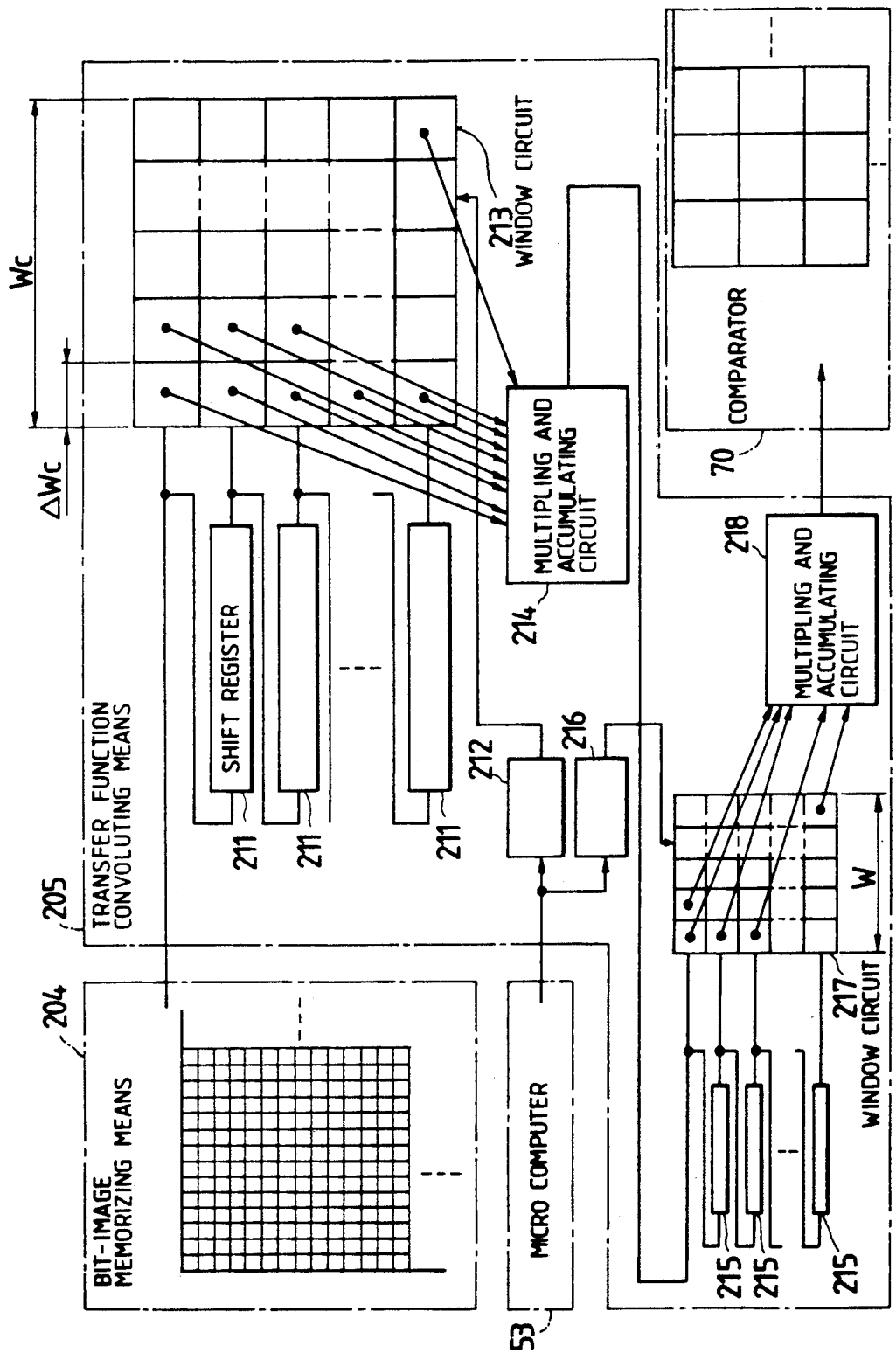
FIG. 19 is a constitution diagram illustrating a transfer function convoluting means.

The transfer function convoluting means 205 is shown in detail in FIG. 19. The transfer function convoluting means 205 comprises a shift register 211, a weight data memory 212, a window circuit 213, a multiplying and accumulating circuit 214, a shift register 215, a weight data memory 216, a window circuit 217 and a multiplying and accumulating circuit 218.

The bit image read in sequence from the bit image memorizing means 204 is cut out through the shift register 211 by amount $N^2$ of the convolution filter, and transmitted to the window circuit 213 having function as the convolution filter calculated by expression (11). The bit image is weighted in the window circuit 213 in accordance with weight data transmitted through the weight data memory 212 from the micro computer 53, and added in the multiplying and accumulating circuit 214. Thus the weighted integral is finished.

Next, in order to calculate the signal level detected by the detector 51 within the inspected reticle inspecting unit 4, calculated value by the multiplying and accumulating circuit 214 is added in area of the same size as the pixel size of the detector 51.

Consequently, Ni of size to be cut out becomes following expression (14).

$$Ni = W/\Delta W \qquad (14)$$

Signal added in the multiplying and accumulating circuit 214 is cut out through the shift register by amount of Ni×Ni.

The cutting-out signal is weighted by the window circuit 217, and added in the multiplying and accumulating circuit 218, and outputted as the standard reticle inspection data to the comparator 70.

In this case, weight of the window circuit 217 calculates characteristics of the filter produced since the CCD is scanned and characteristics of phenomenon called crosstalk that the detected optical signal leaks out of the CCD element.

Then alignment of the reticle and the standard reticle inspection data converting the design data is necessarily accompanied by error $\beta$.

Regarding treatment of the error $\beta$, in similar manner to that described in the first embodiment, processing using expressions (2)∼(7) as described in detail may be performed. Also in this example, the operation principle in the case of detecting a foreign substance having specific size or more only by the detecting system, i.e., only by the binarization is as described in the first embodiment, and the description shall be omitted here.

Figure 18:
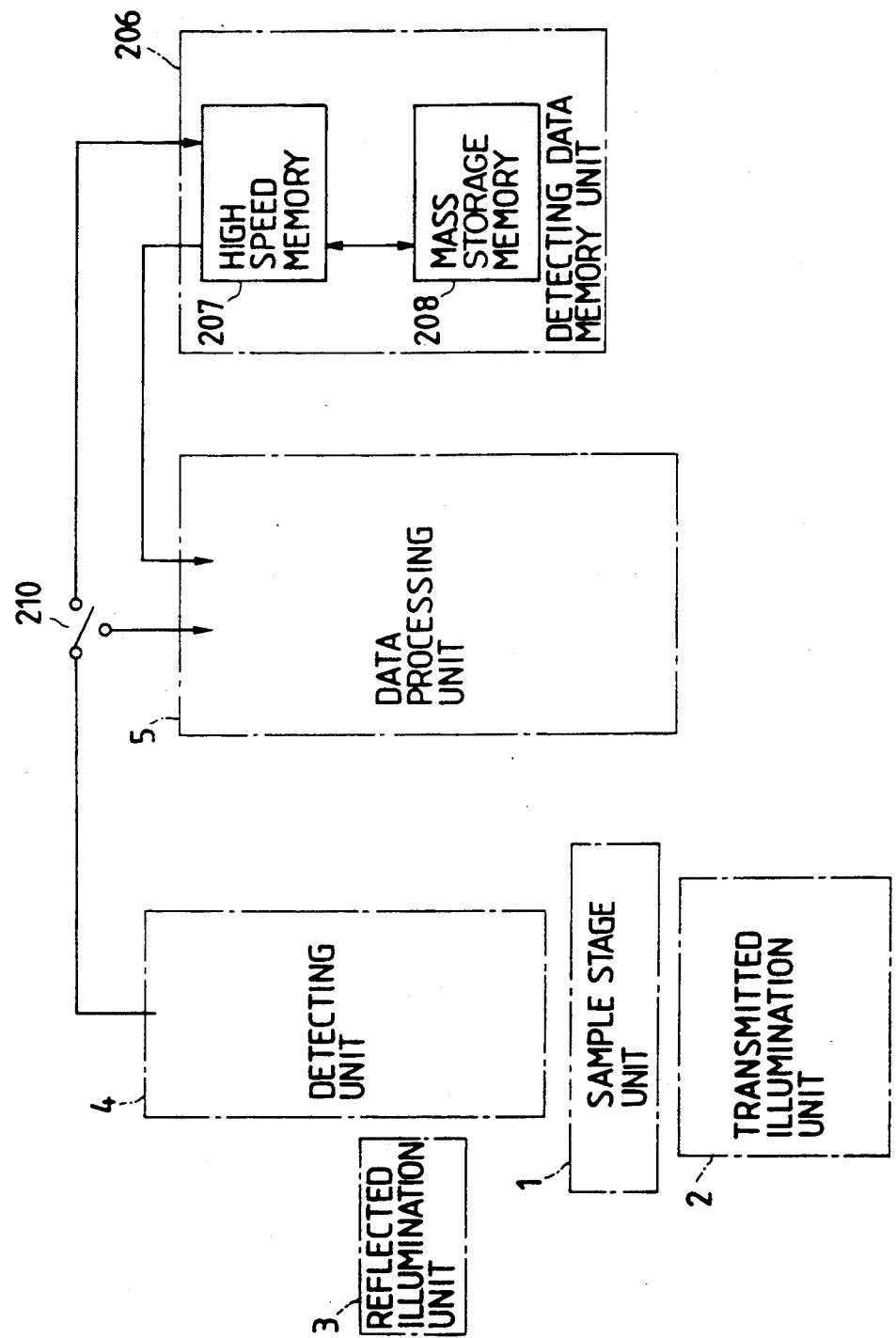
FIG. 18 is a schematic constitution diagram illustrating a third embodiment of the invention.

In place of the standard data generating unit 201 of the second embodiment shown in FIG. 17, in the third embodiment, a standard reticle inspection data memorizing unit 206 shown in FIG. 18 may be used. This is means for detecting the standard reticle in the detecting unit 4 and storing the detected data, and constituted by a mass storage memory 207 such as an optical disk, a hard disk, a magnetic tape, and a high speed memory 208 such as SRAM, DRAM. In the invention, the standard reticle is previously held on the sample holder unit 1, and detection data from the detecting unit 4 is stored through a switch 210 to the standard reticle inspection data memorizing unit 206.

Next, the inspection reticle is held thereon, and detection data from the detecting unit 4 is transmitted through the switch 210 (FIG. 18) to the data processing unit 5 and compared with signal from the standard reticle inspection data memorizing unit 206. During operation of the invention, the standard reticle inspection data memorizing unit 206 is used in place of the standard data generating unit 201. The invention is technology enabled by that the memory of high speed and large capacity can be supplied at low cost.

In any of the embodiments, one detecting unit is used. In this constitution, since distortion of image due to aberration of the detection optical system need not be corrected, false alarm due to misalignment caused by distortion of the image can be decreased.

According to the invention having the above-mentioned constitution, since standard signal equivalent to detection signal of the inspection object by inspection means can be generated from the design data and compared with the detection signal, the detection accuracy, the detection speed and the detection reliability can be improved.

Also according to the present invention, since illumination equivalent optically to illumination of an exposure unit is used and light scattered and diffracted by a foreign substance and a defect and being not incident to a reduction projection lens of the exposure unit can be selectively detected, the detection signal is eliminated from the pattern and the detection signal from the defect or the foreign substance producing actual damage can be actualized and the defect or the foreign substance can be detected.

Since the inspection area on the reticle is limited and the reticle is scanned and the whole inspection area can be inspected, the objective lens having N. A. larger than that of the reduction projection lens in ordinary use can be used.

Further constitution of the illumination system can be simplified, and constitution of the detection system can be also simplified.

What is claimed is:

1. A method of inspecting reticles, comprising:
an inspected reticle inspection step including illuminating light having an adjusted spatial coherency onto an inspected reticle held on a movable inspected reticle stage with an inspected reticle illumination means, collecting transmitted light or reflected light from said inspected reticle with an inspected reticle objective lens and blocking light in the collected light corresponding to the adjusted spatial coherency with an inspected reticle light blocking means installed at a Fourier transformation position of the inspected reticle, and detecting the collected light passing said inspected reticle light blocking means with an inspected reticle detector which converts the detected light into an electric signal;
a standard reticle inspection step including illuminating light having an adjusted spatial coherency onto a standard reticle held on a movable standard reticle stage with a standard reticle illumination means, collecting transmitted light or reflected light from said standard reticle with a standard reticle objective lens and blocking light in the collected light corresponding to the adjusted spatial coherency with a standard reticle light blocking means installed at a Fourier transformation position of the standard reticle, and detecting the collected light passing said standard reticle light blocking means with a standard reticle detector which converts the detected light into an electric signal;
a control step including moving said inspected reticle stage and said standard reticle stage integrally or synchronously with control means; and
a detection step for detecting a defect or a foreign substance on the inspected reticle including comparing the electric signal from said inspected reticle detector with the electric signal from said standard reticle detector so as to eliminate a signal corresponding to a pattern on the inspected reticle and detect a defect or a foreign substance existing on the inspected reticle.

2. A method as set forth in claim 1, wherein each said light blocking means is a light blocking plate.

3. A method as set forth in claim 2, wherein a diameter dm of each said light blocking plate is specified by $$dm = ds \cdot \frac{N.A.}{\sin\theta} \cdot (1 + \delta).$$

4. A method as set forth in claim 2, wherein a diameter dm of each said light blocking plate is specified by $$dm = ds \cdot a(1 + \delta').$$

5. A method of inspecting reticles, comprising:

an inspected reticle inspection step including illuminating light onto an inspected reticle held on a movable inspected reticle stage with an inspected reticle illumination means, collecting transmitted light from said inspected reticle with a detecting optical system, and detecting the collected light with an inspected reticle detector which converts the detected light into an electric signal;

a standard reticle inspection data generating step including converting design data for a pattern into a binary image and processing the binary image with a spatial filter having a transfer function equivalent to a transfer function of the detecting optical system of said inspected reticle inspection step to generate a reference image signal; and a detection step for detecting a defect or a foreign substance on the inspected reticle including comparing the electric signal from said inspected reticle detector with the reference image signal from said standard reticle inspection data generating step so as to eliminate a signal corresponding to a pattern on the inspected reticle and detect a defect or a foreign substance existing on the inspected reticle.

6. An apparatus for inspecting reticles, comprising:

an inspected reticle inspection unit including an inspected reticle illumination means for illuminating light having an adjusted spatial coherency onto an inspected reticle held on a movable inspected reticle stage, an inspected reticle objective lens for collecting transmitted light or reflected light from said inspected reticle, an inspected reticle light blocking means installed at a Fourier transformation position of the inspected reticle for blocking light in the collected light corresponding to the adjusted spatial coherency, and an inspected reticle detector for detecting the collected light passing said inspected reticle light blocking means and converting the detected light into an electric signal;

a standard reticle inspection unit including a standard reticle illumination means for illuminating light having an adjusted spatial coherency onto a standard reticle held on a movable standard reticle stage, a standard reticle objective lens for collecting transmitted light or reflected light from said standard reticle, a standard reticle light blocking means installed at a Fourier transformation position of the standard reticle for blocking light in the collected light corresponding to the adjusted spatial coherency, and a standard reticle detector for detecting the collected light passing said standard light blocking means and converting the detected light into an electric signal;

control means for moving the inspected reticle stage of said inspected reticle inspection unit and the standard reticle stage of said standard reticle inspection unit integrally or synchronously; and detection means for detecting a defect or a foreign substance for comparing the electric signal from the inspected reticle detector of said inspected reticle inspection unit and the electric signal from the standard reticle detector of said standard reticle inspection unit so as to eliminate a signal corresponding to a pattern on the inspected reticle and detect a defect or a foreign substance existing on the inspected reticle.

7. An apparatus as set forth in claim 6, wherein each said light blocking means is a light blocking plate.

8. An apparatus as set forth in claim 7, wherein a diameter dm of each said light blocking plate is specified by $$dm = ds \cdot \frac{N.A.}{\sin\theta} \cdot (1 + \delta).$$

9. An apparatus as set forth in claim 7, wherein a diameter dm of each said light blocking plate is specified by $$dm = ds \cdot a(1 + \delta').$$

10. An apparatus as set forth in claim 6, wherein an aperture of each of the inspected reticle objective lens and the standard reticle objective lens is made larger than an aperture of a reduction projection lens for subjecting the inspected reticle to reduction projection exposure, and the inspected reticle light blocking means and the standard reticle light blocking means are formed so as to block light incident to the aperture of said reduction projection lens.

11. A method of detecting a defect or a foreign substance on a reticle, comprising:

an inspected reticle inspection step including illuminating light having a desired spatial coherency onto an inspected reticle having a circuit pattern formed thereon with illumination means, focusing transmitted light from the inspected reticle with focusing means, shielding light in the focused light corresponding to the desired spatial coherency with light shielding means disposed at a Fourier transformation position of the inspected reticle, and detecting the shielded focused light with a detector which converts the detected light into an image signal, the focusing means and the light shielding means constituting a detecting optical system;

a standard reticle inspection data generating step for generating a reference image signal by processing design data for the circuit pattern formed on the inspected reticle with a spatial filter having a transfer function equivalent to a transfer function of the detecting optical system; and a defect detecting step for detecting a defect or a foreign substance on the inspected reticle including comparing the image signal from the inspected reticle inspection step with the reference image signal from the standard reticle inspection data generating step so as to eliminate a signal corresponding to the circuit pattern formed on the inspected reticle and detect a defect or a foreign substance present on the inspected reticle.

12. A method as set forth in claim 11, wherein the spatial filter corresponds to a point spread function (h(x, y) obtained by performing an inverse Fourier transformation of a transfer function H(u, v) equivalent to a transfer function of the detecting optical system, and wherein a reference image signal g(x, y) is generated from design data f(x, y) for the circuit pattern and the point spread function h(x, y) in accordance with the following equation:

$$g(x, y) = \int \int_{-\infty}^{\infty} f(x', y') \cdot h(x - x', y - y') dx' dy'.$$

13. An apparatus for detecting a defect or a foreign substance on a reticle, comprising:
   inspected reticle inspection means including illuminating means for illuminating light having a desired spatial coherency onto an inspected reticle having a circuit pattern formed thereon, focusing means for focusing transmitted light from the inspected reticle, light shielding means disposed at a Fourier transformation position of the inspected reticle for shielding light in the focused light corresponding to the desired spatial coherency, and a detector for detecting the shielded focused light and converting the detected light into an image signal, the focusing means and the light shielding means constituting a detecting optical system;
   standard reticle inspection data generating means for generating a reference image signal by processing design data for the circuit pattern formed on the inspected reticle with a spatial filter having a transfer function equivalent to a transfer function of the detecting optical system; and
   detecting means for detecting a defect or a foreign substance on the inspected reticle by comparing the image signal from the inspected reticle inspection means with the reference image signal from the standard reticle inspection data generating means so as to eliminate a signal corresponding to the circuit pattern formed on the inspected reticle and detect a defect or a foreign substance present on the inspected reticle.

14. An apparatus as set forth in claim 13, wherein the illuminating means includes light source means for producing light, diffusing means for diffusing the light produced by the light source means, aperture means for restricting the diffused light from the diffusing means to a desired optical flux, and collimating means for focusing the desired optical flux from the aperture means;
   wherein the focusing means focuses light from the collimating means scattered by a defect or a foreign substance present on the inspected reticle; and
   wherein the light shielding means passes light having a high spatial frequency scattered by the defect or the foreign substance on the inspected reticle in the focused light from the focusing means.

15. An apparatus as set forth in claim 14, further comprising a phase filter included in the detecting optical system.

16. An apparatus as set forth in claim 14, wherein the standard reticle inspection data generating means includes bit-image forming means for forming a binary image, bit-image memory means for storing the binary image, means for reading out the binary image stored in the bit-image memory means, and transfer function convolution means for weighting the binary image read out from the bit-image memory means to produce the reference image signal.

17. An apparatus as set forth in claim 16, wherein the transmission function convolution means includes a plurality of weighting means.

18. An apparatus as set forth in claim 13, wherein the spatial filter corresponds to a point spread function h(x, y) obtained by performing an inverse Fourier transformation of a transfer function H(u, v) equivalent to a transfer function of the detecting optical system, and wherein a a reference image signal g(x, y) is generated from design data f(x, y) for the circuit pattern and the point spread function h(x, y) in accordance with the following equation:

$$g(x, y) = \int \int_{-\infty}^{\infty} f(x', y') \cdot h(x - x', y - y') dx' dy'.$$

* * * * *